(12) United States Patent
Jackson

(10) Patent No.: US 6,202,272 B1
(45) Date of Patent: Mar. 20, 2001

(54) HAND-HELD STENT CRIMPING DEVICE

(75) Inventor: Gregg A. Jackson, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/032,472

(22) Filed: Feb. 26, 1998

(51) Int. Cl.[7] ................................................ B23P 19/02
(52) U.S. Cl. .................... 29/235; 29/234; 29/268; 29/270; 29/282; 29/283.5; 81/3.43; 81/64
(58) Field of Search ........................... 29/282, 283.5, 29/268, 234, 235, 270, 751, 516, 280; 294/31.2; 81/3.43, 64; 269/130–132; 606/139, 140, 194, 108

(56) References Cited

U.S. PATENT DOCUMENTS

| | | | |
|---|---|---|---|
| 698,492 | * | 4/1902 | Hart ........................................ 81/3.43 |
| 5,295,420 | * | 3/1994 | Grimes .................................. 81/3.43 |
| 5,920,975 | * | 7/1999 | Morales ................................ 29/282 |
| 5,931,851 | * | 8/1999 | Morales ................................ 29/235 |

* cited by examiner

*Primary Examiner*—Robert C. Watson
(74) *Attorney, Agent, or Firm*—Fulwider Patton Lee & Utecht, LLP

(57) ABSTRACT

A device for enabling substantially uniform and tight crimping of an intravascular stent onto a balloon catheter assembly. The stent crimping device includes at least one compressible and resiliently expandable loop portion, that is expandable radially outwardly to enable supporting of the stent and catheter assembly thereon, and compressible radially inwardly to substantially uniformly and tightly crimp the stent onto the balloon catheter assembly.

11 Claims, 3 Drawing Sheets

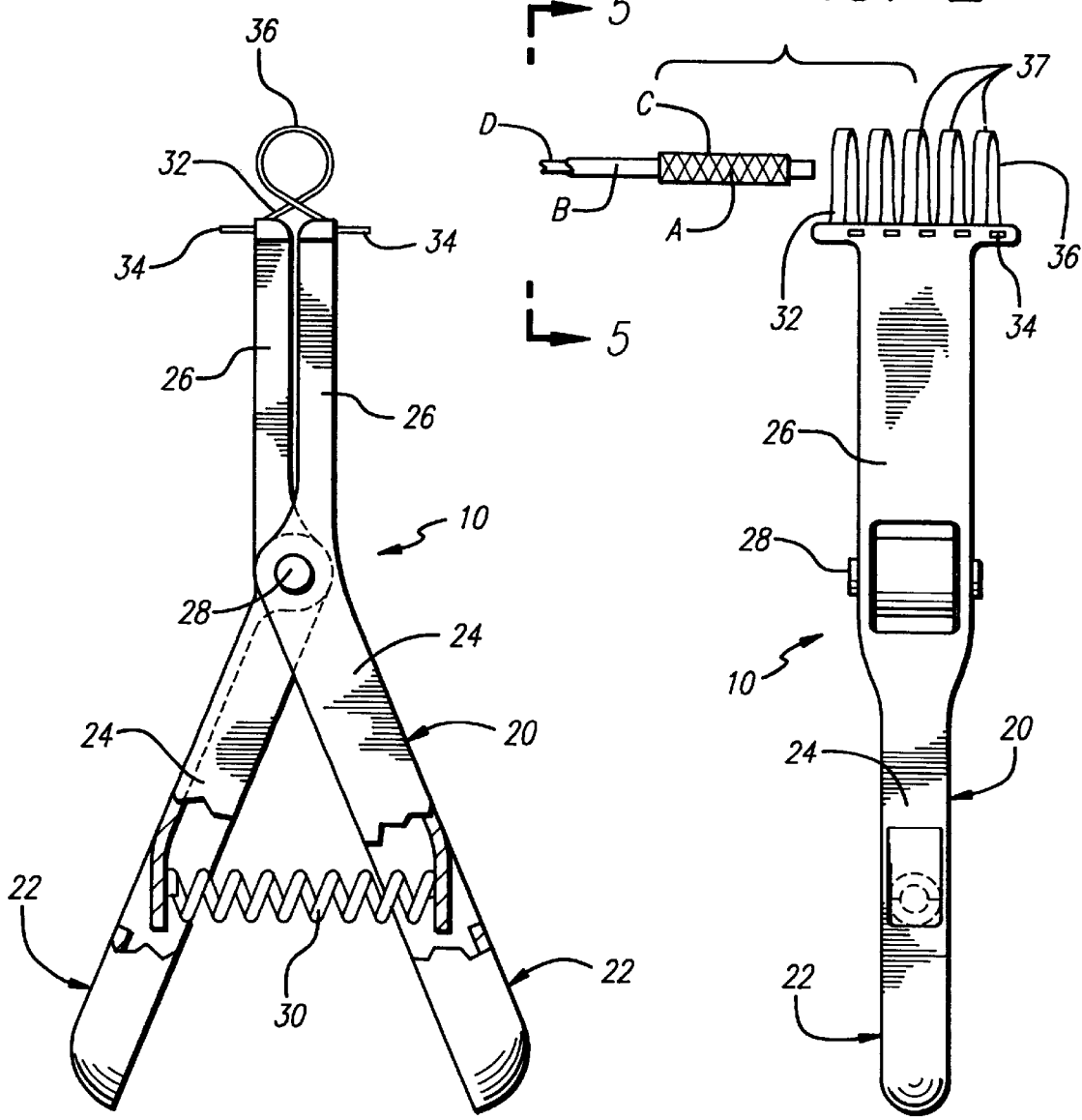
FIG. 2
FIG. 1
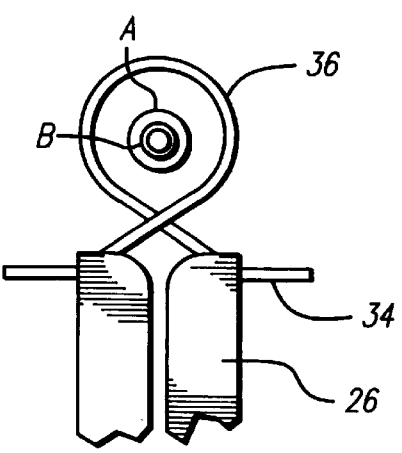
FIG. 5

HAND-HELD STENT CRIMPING DEVICE

BACKGROUND OF THE INVENTION

1. Field of the Invention

This invention relates to a stent crimping device of the type that will enable the user to crimp a stent onto the distal end of a balloon dilatation catheter assembly, for example of the kind used in a typical percutaneous transluminal coronary angioplasty (PTCA) procedure.

2. Description of the Related Art

In a typical PTCA procedure, for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A guidewire and a dilatation catheter having a balloon on the distal end are introduced through the guiding catheter with the guidewire sliding within the dilatation catheter. The guidewire is first advanced out of the guiding catheter into the patient's coronary vasculature, and the dilatation catheter is advanced over the previously advanced guidewire until the dilatation balloon is properly positioned across the lesion. Once in position across the lesion, a flexible, expandable, preformed balloon is inflated to a predetermined size with radiopaque liquid at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, a restenosis of the artery may develop over several months, which may require another angioplasty procedure, a surgical bypass operation, or some method of repairing or strengthening the area. To reduce the chance of the development of restenosis and strengthen the area, a physician can implant an intravascular prosthesis for maintaining vascular patency, typically called a stent. A stent is a device used to hold tissue in place in a vessel or to provide a support for a vessel to hold it open so that blood flows freely. A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion.

However, if the stent is not tightly crimped onto the catheter balloon portion, when the catheter is advanced in the patient's vasculature the stent may move or even slide off the catheter balloon portion in the coronary artery prior to expansion, and may block the flow of blood, requiring procedures to remove the stent.

In procedures where the stent is placed over the balloon portion of the catheter, the stent must be crimped onto the balloon portion to prevent the stent from sliding off the catheter when the catheter is advanced in the patient's vasculature. In the past this crimping was often done by hand, which does not provide optimum results due to the uneven force being applied, resulting in non-uniform crimps. In addition, it was difficult to judge when a uniform and reliable crimp had been applied. Though some tools, such as ordinary pliers, have been used to apply the stent, these tools have not been entirely adequate in achieving a uniform crimp. Moreover, an unevenly crimped stent may result in an unevenly expanded stent in the vessel or artery, which is undesirable.

SUMMARY OF THE INVENTION

This invention is directed to a vascular prosthesis crimping device which enables substantially uniform and tight crimping of a stent onto a catheter balloon portion, to better secure the stent onto the catheter for delivery of the stent through the patient's vasculature.

The present invention attempts to solve several problems associated with crimping stents onto balloon catheters.

In an exemplary embodiment of the present invention, the stent crimping device includes a compressible and resiliently expandable loop portion (e.g., mylar, nylon, nickel-titanium (NiTi), polymide) in the tip of a hand tool (or mechanical device such a a pneumatic cylinder), connected to the distal end of jaw portions of the hand tool. The loop portion is compressible radially inwardly by the application of compressive force to the hand tool by the user, to substantially uniformly and tightly crimp the stent onto the balloon catheter assembly. The loop portion is further expandable upon release by the user of the compressive force applied to the hand tool, to enable the loop portion to resiliently expand for enabling another stent and balloon catheter assembly to be supported therein for crimping.

The device enables the stent to be crimped onto the distal end of a balloon catheter substantially uniformly and tightly, reducing the risk that the stent may slide off the catheter balloon portion. It is further easy to use in performing the stent crimping procedure. It also enables the crimping procedure to be repeatably performed on stent and balloon catheter assemblies with substantially repeatable crimping force applied thereto.

These and other advantages of the invention will become more apparent from the following detailed description thereof when taken in conjunction with the accompanying drawings.

BRIEF DESCRIPTION OF THE DRAWINGS

FIG. 1 is a side elevational view of an exemplary embodiment of the present invention, in which the loop portion of the hand tool is in expanded condition for supporting the stent positioned on the catheter balloon portion.

FIG. 2 is an elevational view of the exemplary embodiment of the present invention in the expanded loop portion condition as shown in FIG. 1.

FIG. 5 is an elevational partly-fragmentary end view of the stent and balloon catheter supporting member, prior to crimping the stent onto the balloon catheter, taken along line 5—5 in FIG. 2.

DETAILED DESCRIPTION OF THE PREFERRED EMBODIMENTS

Figure 3:
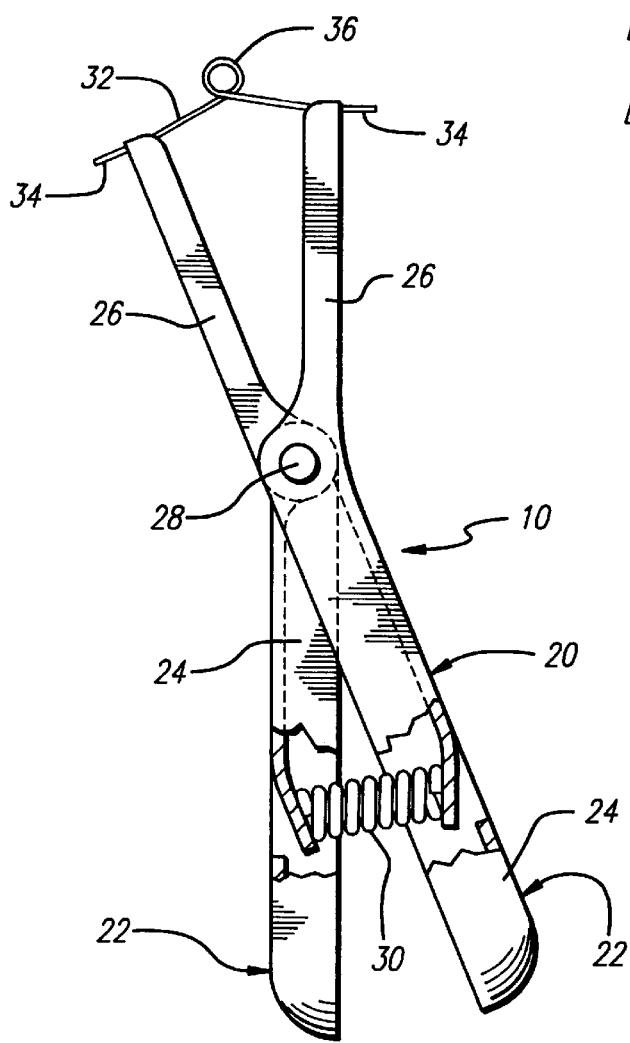
FIG. 3 is a side elevational view of the exemplary embodiment of the present invention in which the loop portion of the hand tool is in compressed condition for substantially uniformly and tightly crimping the stent onto the catheter balloon portion.

Device 10 comprises a tool 20 for enabling substantially uniform and tight crimping of an intravascular stent A onto the collapsed balloon portion B adjacent to the distal end C of a balloon catheter assembly D. In the exemplary embodiment of device 10, as shown in FIGS. 1–4, tool 20 is adapted to be held in the hand of the user, so as to enable stent A and catheter D to be supported in tool 20, and to enable the user to apply compressive force to tool 20 to substantially uniformly and tightly crimp stent A on catheter D.

Tool 20 includes a pair of arms 22, each arm 22 having handle portions 24 and opposed jaw portions 26. The arms are pivotally interconnected by pivot pin 28, and normally held in expanded condition by coil spring 30. Spring 30 extends between and biases handle portions 24 in normally expanded condition, biasing jaw portions 26 and connecting portions 34 in normally compressed condition and loop portion 36 in normally expanded condition. Spring 30 comprises a compressed spring. In the expanded condition of handle portions 24, jaw portions 26 are compressed, and in a compressed condition of handle portions 24, jaw portions 26 are expanded.

Tool 20 further includes a crimping member 32, connected to the distal ends of jaw portions 26, for supporting stent A and catheter D therein. Member 32 includes portions 34 for connecting supporting member 32 to jaw portions 26, and at least one compressible loop portion 36 wherein the portion of balloon catheter assembly D with stent A loaded thereon may be supported. Supporting member 32 is comprised of compressible and resiliently expandable material, such that upon expansion of jaw portions 26 by compression of handle portions 24, jaw end portions 34 are expanded and loop portion 36 is compressed radially inwardly to substantially uniformly and tightly crimp stent A onto catheter D (or any stent delivery device). Upon compression of jaw portions 26, by releasable expansion of handle portions 24, distal jaw end portions 34 are drawn together and loop portion 36 is expanded radially outwardly to support stent A and balloon catheter portion B therein.

Figure 4:
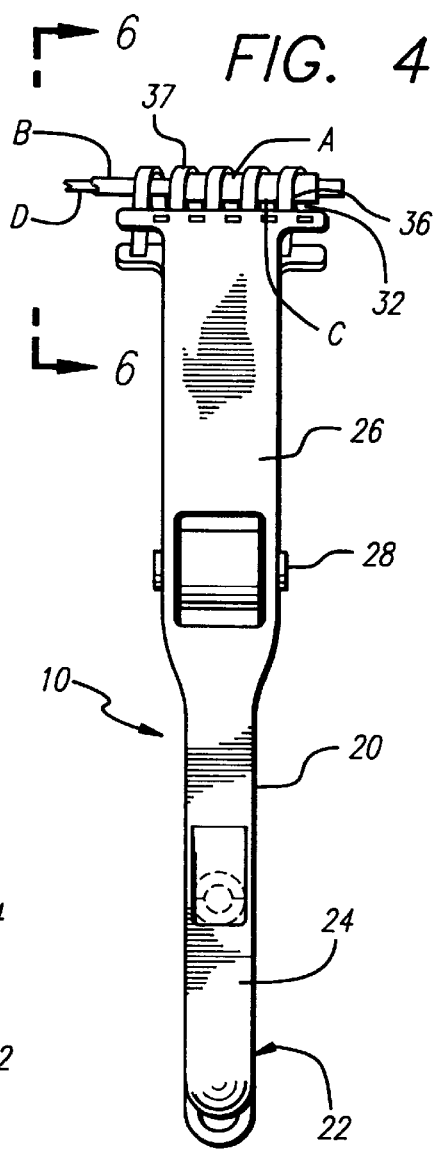
FIG. 4 is an elevational view of the exemplary embodiment of the present invention in compressed loop portion condition as shown in FIG. 3.
Figure 6:
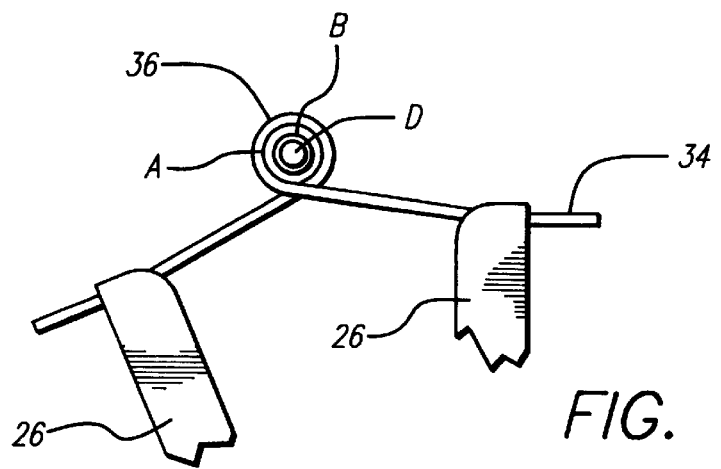
FIG. 6 is similar to the FIG. 5 view, after crimping the stent onto the balloon catheter.

In one embodiment as shown in FIGS. 2 and 4, loop portion 36 comprises a tubular sleeve including a plurality of discrete spaced apart interconnected loops 37, wherein the length of the sleeve is at least as long as the length of stent A and the diameter of the sleeve is greater than the diameter of stent A. Alternatively, the sleeve may comprise a continuous tubular or cylindrical loop portion 36. FIGS. 2 and 4 depict loops 37 having a rectangular cross-section such as in a ribbon. Alternatively, loop portion 36 may be formed from a wire having a round cross-sectional shape, or other cross-sectional shapes known in the art.

The sleeve may also include a slotted mount, to enable tightening or loosening thereof dependent upon the size profiles of catheter D and stent A to be crimped thereon.

Member 32 may comprise a threaded-capstan-sleeve configuration, or alternatively a wire loop or plurality of wire loops, such as a guitar-string-type mechanism for tightening or loosening the sleeve depending upon the profile and material of catheter balloon portion B on which stent A is to be crimped, for enabling tighter crimping.

In operation, to load stent A onto collapsed balloon portion B of balloon catheter assembly D, catheter balloon portion B is inserted in stent A so that stent A overlies balloon portion B. To enable stent A to be crimped onto catheter balloon portion B or other mechanism for delivering or deploying a stent, stent A and catheter balloon portion B may be inserted into and supported in the middle of loop portion 36 of tool supporting member 32. At this point, stent A is not crimped onto catheter assembly D, because stent A has not been compressed.

To crimp stent A onto catheter balloon portion B, the user of tool 20 compresses handle portions 24 together against the biasing force of compressed spring 30. As handle portions 24 are compressed, jaw portions 26 and connecting portions 34 expand, and loop portion 36 compresses radially inwardly, compressing stent A radially inwardly and tightly onto catheter balloon portion B at a substantially uniform rate.

If further crimping of stent A onto catheter balloon portion B is desired, the user may rotate the crimped stent A and catheter balloon portion B and/or move them forward or backward in loop portion 36, and repeat the crimping procedure until stent A is as tightly crimped on catheter balloon portion B as desired.

After stent A has been crimped onto catheter balloon portion B, the user may release handle portions 24, which expand under the biasing force of compressed spring 30. As handle portions 24 expand, jaw portions 26 and connecting portions 34 compress, and loop portion 36 expands radially outwardly, enabling removal of the crimped stent and catheter balloon portion from loop portion 36. Balloon catheter assembly D, with stent A crimped thereon, may then be inserted into the body of the patient for deployment of stent A therein.

Figure 7:
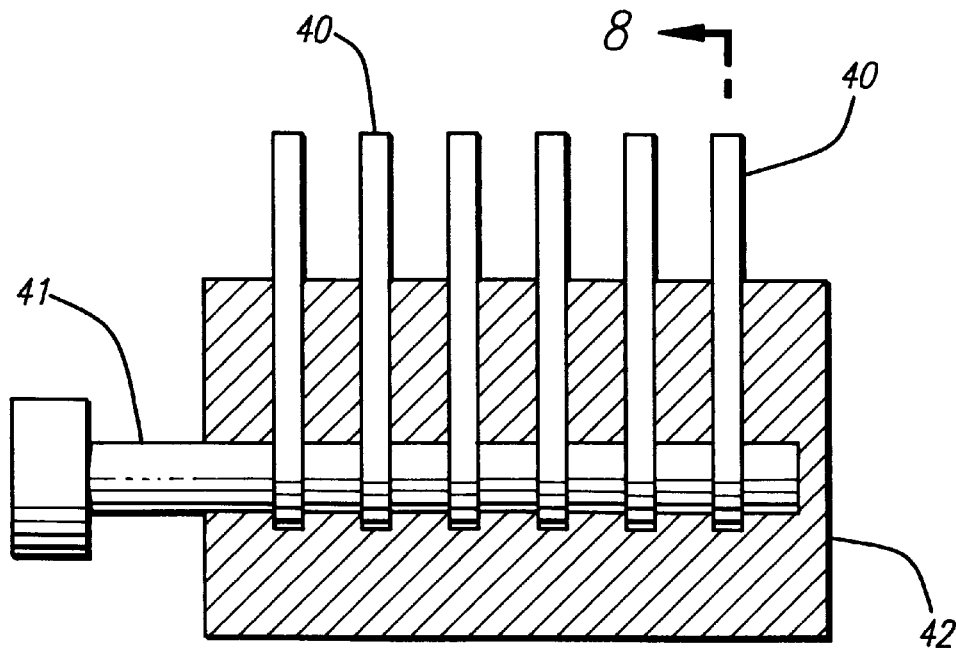
FIG. 7 is a partial cross-sectional view depicting another embodiment of the invention where a plurality of loops are tightened by a thumbscrew to compress the stent onto the distal end of the catheter.
Figure 8:
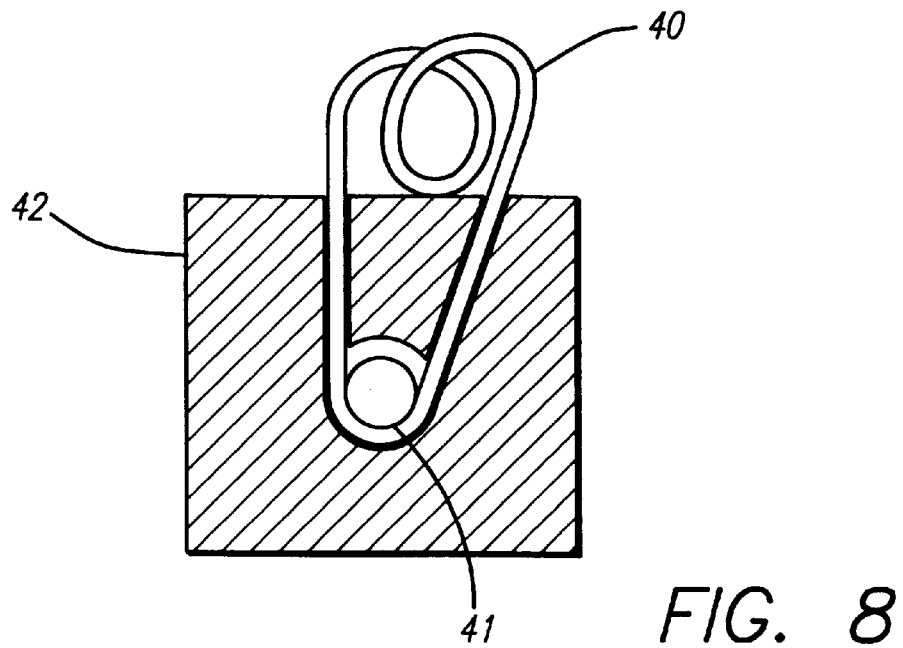
FIG. 8 is a cross-sectional view taken along lines 8—8 depicting the wire loops of FIG. 7.

In another embodiment of the invention, as depicted in FIGS. 7 and 8, a plurality of wire loops 40 are wound around thumbscrew 41. A thumbscrew 41 is tightened, for example by hand, wire loops 40 will become smaller. Support member 42 supports thumbscrew 41 and provides a basis for the thumbscrew threads to engage and tighten and draw down wire loops 40. As the diameter of wire loops 40 decrease, a stent mounted on the balloon portion of the catheter, as depicted in prior drawing figures, can be inserted in the loops and compressed onto the balloon portion of the catheter. The amount of force applied in crimping the stent is a matter of choice. The embodiment of FIGS. 7 and 8 can be incorporated into the device depicted in FIGS. 1–6.

While in the preferred embodiment the stent described is intended to be an intraluminal vascular prosthesis for use within a blood vessel, and the balloon delivery catheter is of the same as or similar to that used in therapeutic coronary angioplasty, it will be appreciated by those skilled in the art that modifications may be made to the present invention to allow the present invention to be used to load any type of prosthesis. The present invention is not limited to stents that are deployed in a patient's vasculature, but has wide applications to loading any type of graft, prosthesis, liner or similar structure. Furthermore, the stent may be delivered not only into coronary arteries, but into any body lumen. Other modifications can be made to the present invention by those skilled in the art without departing from the scope thereof.

What is claimed is:

1. A device for crimping a stent onto a balloon catheter or other stent delivery assembly, comprising:

means for supporting a portion of the balloon catheter assembly on which the stent may be loaded, including a compressible portion including a plurality of loops with opposed ends which loops are substantially uniformly compressible radially inwardly upon the application of force thereto to substantially uniformly and tightly crimp the stent onto the catheter portion, and is resiliently expandable radially outwardly upon release of the applied force to support the stent and catheter portion therein; and means for enabling force to be applied to the supporting means including a pair of pivotally connected handles having jaws, wherein the opposed ends of the plurality of loops are attached to the jaws, adapted to be held in the hand of the user so as to enable the user to apply compressive force thereto to generate substantially uniform compression, radially inwardly, of the compressive portion of the supporting means, for substantially uniformly and tightly crimping the stent onto the catheter portion.

2. A device as in claim 1, further comprising means for biasing the force applying means so as to bias the compressible portion of the supporting means in normally expanded condition.

3. A device as in claim 1, wherein the supporting means comprise a wire, and the compressible portion comprises a plurality of loops supporting the stent and catheter portion and enabling substantially uniform and tight crimping of the stent onto the catheter portion.

4. A device as in claim 1, wherein the force application enabling means comprise a pair of pivotally connected arms, each including a handle portion and an opposed jaw portion, means for pivotally connecting the pair of arms together such that upon expanding the handle portions the jaw portions compress, and upon releasing compression of the handle portions the jaw portions expand, and means for connecting the supporting means to the jaw portions such that upon releasing compression of the jaw portions the compressible portion of the supporting means compress, and upon compressing the jaw portions the compressible portion of the supporting means expand.

5. A device as in claim 2, wherein the biasing means comprise a compressed spring.

6. A device as in claim 1, further comprising means for enabling adjustment of the size of the plurality of loops dependent upon the size of the stent and catheter portion to be supported therein.

7. A device as in claim 4, wherein the supporting means further comprise portions for connecting the supporting means to the connecting means.

8. A device as in claim 4, further comprising means for biasing the handle portions in normally expanded condition.

9. A device as in claim 8, wherein the biasing means comprise a compressed spring.

10. A device for crimping a stent onto the expandable portion of a catheter, comprising:
   a pair of handles pivotally connected at a common hinge to a pair of opposed jaws;
   a wire having a rectangular cross-section and having a plurality of loops and disposed between and attached to the opposed jaws;
   a spring disposed between the pair of handles for biasing the handles apart, whereby application of force to close the handles causes the opposed jaws to pivotally move apart so that the at least one wire loop becomes smaller in diameter.

11. A device as in claim 10, wherein the diameter of the at least one wire loop is adjustable for receiving stents and catheters of various dimensions.

* * * * *

UNITED STATES PATENT AND TRADEMARK OFFICE
CERTIFICATE OF CORRECTION

PATENT NO. : 6,202,272 B1
DATED : March 20, 2001
INVENTOR(S) : Greg A. Jackson

It is certified that error appears in the above-identified patent and that said Letters Patent is hereby corrected as shown below:

Title page,
Under "U.S. PATENT DOCUMENTS", add the following:
    -- 2,452,857    11/1948    Mesaros
       4,907,336    3/1990     Gianturco
       5,132,066    7/1992     Charlesworth, et al.
       5,133,732    7/1992     Witkor
       5,183,085    2/1993     Timmerman
       5,209,143    5/1993     Sweet --.

Title page,
After "5,931,851 * 8/1999 Morales", add -- FOREIGN PATENT DOCUMENTS
            0 873 371 A 10/1998 EP --.

Column 5,
Lines 24 through 27, claim 3, delete four lines of text beginning with " and the compressible...".
Line 29 and 30, claim 4, delete " a pair of pivotally connected arms each including a handle portion and an opposed jaw portion".
Line 31, change "arms", to read -- handles --.
Lines 32 and 33, change "handle portions the jaw portions", to read -- handles the jaws--
Line 34, change "handle portions the jaw portions", to read -- handle the jaws --.
Line 35, change, "jaw portions", to read -- jaws --.

Column 6,
Line 1, change "jaw portions", to read -- jaws --.
Line 3, change "jaw portions", to read -- jaws --.

Signed and Sealed this

Twenty-third Day of October, 2001

*Attest:*

*Attesting Officer*

NICHOLAS P. GODICI
*Acting Director of the United States Patent and Trademark Office*